(12) United States Patent
Strisower

(10) Patent No.: US 8,415,143 B2
(45) Date of Patent: Apr. 9, 2013

(54) RACEWAYS FOR PRODUCING MICROALGAE SPECIES

(75) Inventor: John Strisower, Chico, CA (US)

(73) Assignee: Cleanergy Corp., Chico, CA (US)

( * ) Notice: Subject to any disclaimer, the term of this patent is extended or adjusted under 35 U.S.C. 154(b) by 437 days.

(21) Appl. No.: 12/626,493

(22) Filed: Nov. 25, 2009

(65) Prior Publication Data

US 2011/0124092 A1    May 26, 2011

(51) Int. Cl.
*C12M 1/00* (2006.01)
*C12N 1/12* (2006.01)

(52) U.S. Cl.
USPC .............. 435/292.1; 435/257.1; 435/289.1

(58) Field of Classification Search ............... 435/257.1, 435/289.1, 292.1
See application file for complete search history.

(56) References Cited

U.S. PATENT DOCUMENTS

2012/0129245 A1\* 5/2012 Neeb et al. ............ 435/257.1

\* cited by examiner

*Primary Examiner* — Herbert J Lilling

(57) ABSTRACT

A system for producing a hydrocarbon-producing photosynthetic organism. The system comprises a substantially closed conduit system enclosing a fluid, a fluid-moving mechanism adapted to move the fluid through at least a portion of the conduit system, and a harvester adapted to remove at least a portion of the hydrocarbon-producing photosynthetic organisms from the fluid. The fluid contains a population of a hydrocarbon-producing photosynthetic organism and the conduit system configured to permit at least a portion of the population to receive light suitable for photosynthesis.

13 Claims, 4 Drawing Sheets

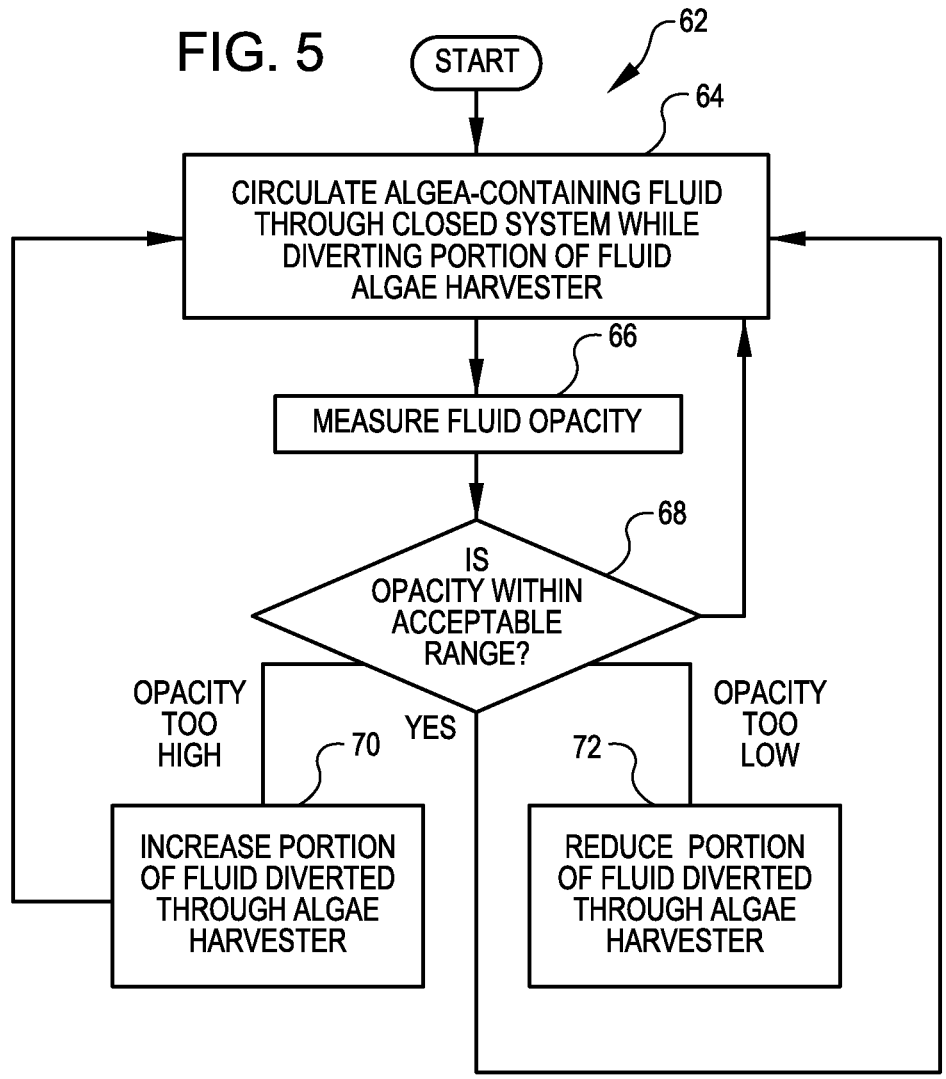

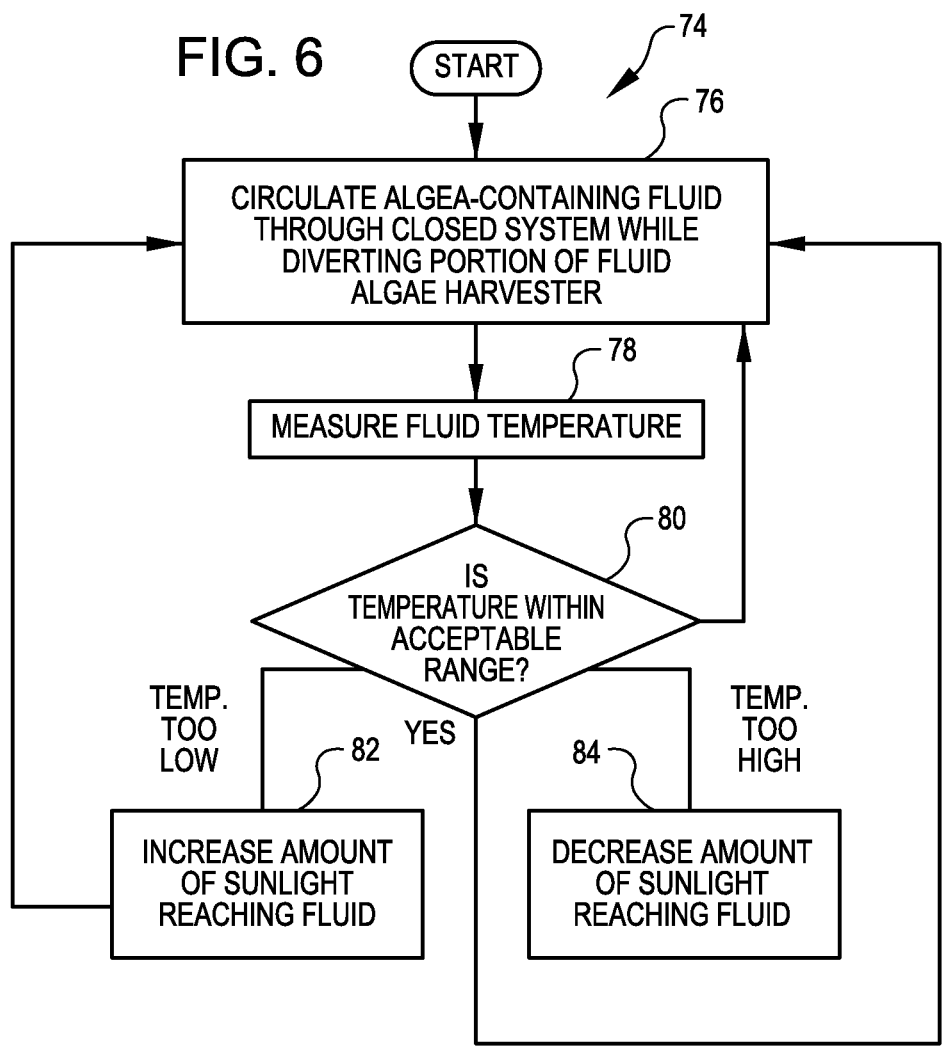

RACEWAYS FOR PRODUCING MICROALGAE SPECIES

BACKGROUND

Much of the global economy depends on petroleum products, the price of which can be very volatile depending on political and economic conditions. This volatility creates a number of issues, including economic issues and national security issues. As a result, many have been searching for and developing alternative forms of energy, such as by improving current methods of extracting energy from coal, wind, and the sun. Biological material has also been identified as a promising source of energy. For example, oil palm and jatropha plants are known to produce seeds with high percentages of oil that can be extracted and refined for fuel.

One promising biological source of oil involves the harvesting of certain species of algae that produce large amounts of oil that can be extracted. Predictions have been made that using harvesting oil from algae can yield amounts of energy several times greater than what is possible using other organisms. Despite these theoretical predictions, the harvesting of algae has yet to become economically viable because the price of harvesting algae has not yet reached a level comparable to other forms of energy. Some of the problems with harvesting algae are caused from the fact that algae typically grows in water and creates stored energy in the form of oil through the process of photosynthesis. As a result, algae tends to float to the surface of bodies of water in which it is grown, thereby causing algae near the surface to grow well whereas algae below the surface do not grow well because they do not have enough sunlight. Consequently, oil yield per unit area typically depends on the surface area of the bodies of water used to grow the algae and much of the volume of the water below the surface is essentially wasted.

SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

In accordance with an embodiment, a system for producing a hydrocarbon-producing photosynthetic organism is provided. The system includes a fluid containing a population of the hydrocarbon-producing photosynthetic organism, a closed raceway, a pump for moving the population through the raceway, and a harvester configured to remove a portion of the population from the fluid. The raceway is configured to contain a portion of the fluid and to permit the portion of the fluid to receive light suitable for photosynthesis by the hydrocarbon-producing photosynthetic organism A method for producing a hydrocarbon-producing photosynthetic organism is also disclosed. The method includes circulating a fluid through a substantially closed conduit system, providing light to the fluid, and removing at least a portion of the population from the system. The fluid contains a population of a hydrocarbon-producing photosynthetic organisms and the light provided to the fluid is suitable for photosynthetic use by the population.

A system is provided for producing a hydrocarbon-producing photosynthetic organism in accordance with yet another embodiment. The system comprises a substantially closed conduit system enclosing a fluid, a fluid-moving mechanism adapted to move the fluid through at least a portion of the conduit system, and a harvester adapted to remove at least a portion of the hydrocarbon-producing photosynthetic organisms from the fluid. The fluid contains a population of a hydrocarbon-producing photosynthetic organisms and the conduit system is configured to permit at least a portion of the population to receive light suitable for photosynthesis.

For a fuller understanding of the nature and advantages of the present invention, reference should be made to the ensuing detailed description and accompanying drawings. Other aspects, objects and advantages of the invention will be apparent from the drawings and the detailed description that follows.

BRIEF DESCRIPTION OF THE DRAWINGS

FIG. 5 shows a continuous algae production method in accordance with another embodiment; and FIG. 6 shows a temperature-controlled algae production method in accordance with yet another embodiment.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Figure 1:
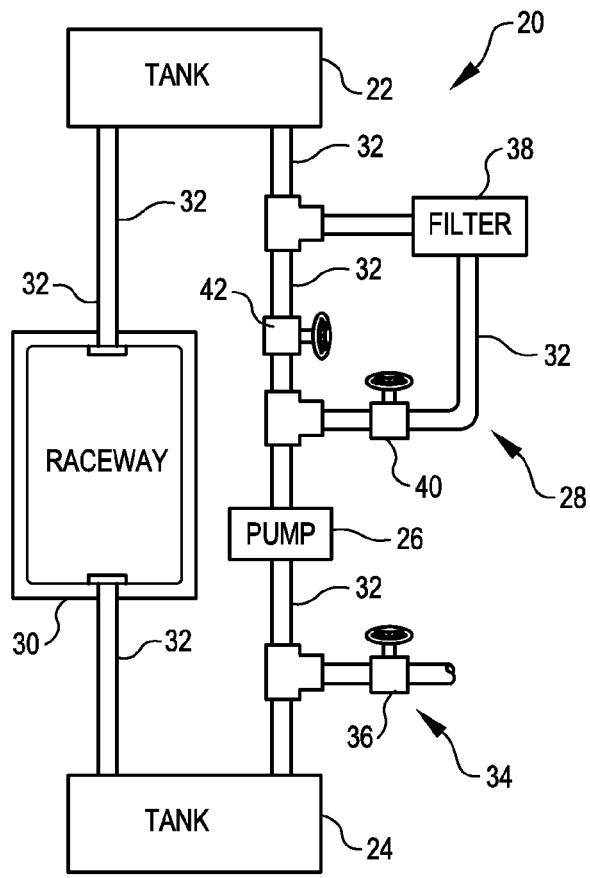
FIG. 1 shows a schematic diagram of a algae production system in accordance with an embodiment.

Referring now to the drawings, in which like reference numerals represent like parts throughout the several views, FIG. 1 shows an algae production system 20 in accordance with an embodiment. Generally, the algae production system 20 is a system configured for the growing and harvesting of algae, in particular hydrocarbon-producing microalgae. However, the algae production system 20 can be used to grow and harvest any hydrocarbon-producing photosynthetic organism and/or microorganism such as suitable bacteria and/or cyanobacteria and, generally, any organism suitable for growing in the disclosed system and not necessarily limited to organisms harvested for hydrocarbons. In an embodiment, the algae production system 20 is a closed system through which a fluid, such as water, containing microalgae is circulated and provided sunlight to enable the microalgae to reproduce. Circulating the fluid throughout the system provides an advantage in that algae in the fluid is stirred in the process, thereby preventing algae from migrating to the surface of the fluid and blocking light from algae not at the surface. In this manner, portions of the algae production system 20 through which sunlight can travel are more effectively utilized because light is able to penetrate deep into the fluid, thereby providing energy for photosynthesis for algae at all levels of the fluid instead of primarily at the surface of the fluid. Thus, circulating the fluid throughout the algae production system 20 allows for greater yields of algae than possible by letting algae grow in stagnant fluid.

As used herein, "closed" means substantially separated from a surrounding environment. Thus, a closed system is a system throughout which the fluid inside the system is substantially separated from an outside environment. As described more fully below, a closed system is provided by circulating the fluid through a plurality of pipes, although other ways of providing a closed system, such as enclosing an open system inside a closed structure that allows sunlight in, can also be used.

Using a closed system provides an advantage in that it allows substantial or total control over the contents of the closed system. For instance, temperature and other factors influencing the rate of algae reproduction can be controlled in a closed system. In addition, a closed system prevents fluid loss through evaporation and helps prevent the introduction of contaminants, such as contaminant species of algae or other organisms that can harm hydrocarbon-producing algae or the production thereof, and other contaminants that can adversely affect the rate of algae production. As another advantage, a closed system can be maintained at a temperature suitable for reproduction of a desired hydrocarbon-producing photosynthetic organism, but lethal to contaminant organisms native to an environment surrounding the closed system. Thus, if a contaminant organism is inadvertently introduced into the closed system, the temperature of the closed system would not allow the contaminant organism to be effective in contaminating the system and significantly harming production of the desired organism. As a specific example, Neochloris Oleoabundans is a species of hydrocarbon-producing microalgae native to the Sahara that can be sustained in a closed system maintained around 120 degrees Fahrenheit, where the closed system is in an environment, such areas near Chico, Calif., where native algae species typically cannot survive for long periods of time at such a temperature. Other suitable species may include strains isolated from desert sands which are evolutionarily evolved to thrive in relatively high temperatures. Other advantages of using one or more heat-tolerant algae species include the ability to maintain a closed system while expending less energy on cooling the system than would be necessary with other hydrocarbon-producing species that may require cooler temperatures.

In the embodiment shown in FIG. 1, the algae production system 20 includes a first tank 22, a second tank 24, a pump assembly 26, a harvesting assembly 28, and a raceway assembly 30. In an embodiment, the first tank 22, second tank 24, pump assembly 26, harvesting assembly 28, and raceway assembly 30 are connected in series with a system of piping 32 as described more fully below. As shown in FIG. 1, the first tank 22 and second tank 24 are separated and fluidly connected by the raceway assembly 30, and piping 32 on one side and fluidly connected by the pump assembly 26, harvesting assembly 28, and piping 32 on another side, so as to form a complete fluidly-connected circuit. The first tank 22 may be at a higher elevation than the second tank 24, although the first tank 22 may be at a lower elevation than the second tank 24 or the first tank 22 and second tank 24 may be at the same elevation. In an embodiment where the first tank 22 is at a higher elevation than the second tank 24, the pump assembly 26 may move water uphill from the second tank 24 to the first tank 22 while water from the first tank 22 flows downhill via gravity through the raceway assembly 30. Further, the pump assembly 26 is any mechanism capable of circulating fluid through the algae production system 20. The pump assembly 26, for instance, can include one or more pumps, paddles, conveyors, or other mechanisms for moving fluid, or combinations thereof.

The algae production system 20 may also include additional features such as an input conduit 34 which may include a portion of piping 32 connected having a first valve 36 configured to selectively provide a fluid connection between the input conduit 34 and the remainder of the production system 20. In this manner, water, nutrients, or any other desired substance can be introduced into the algae production system 20 by opening the first valve 36 and pumping the water, nutrients, or other substance into the algae production system 20 through the input conduit 34. Various items can also be introduced into the algae production 20 through the first tank 22 or second tank 24, for example, by opening the tanks and introducing the substances. Further, levels of various chemicals and organisms in the fluid inside the algae production system 20 can be monitored, through manual and/or automated means, in order to determine what substances and how much of each substance needs to be added through the input conduit 34.

It should be understood that, while FIG. 1 shows the algae production system 20 having its various components in a circuit in a particular order, the order of the components can be varied. For example, the pump assembly 26 need not be located adjacent to the first tank 22, but can be located at any other location in the algae production system 20. In addition, various components of the algae production system 20 may not be necessary. For instance, in an embodiment, the second tank 24 is replaced by piping 32. Generally, if the algae production system 20 minus the tanks contains enough volume, for example, 5,000 gallons or another suitable volume, tanks may be omitted altogether. Also, while FIG. 1, for the sake of illustration, shows the algae production system 20 having one of each component, more than one of each component can be included. Thus, the algae production system 20 can, for example, have multiple harvesting assemblies, multiple pump assemblies, and/or multiple raceway assemblies.

As shown in FIG. 1, the harvesting assembly 28 may include a filter assembly 38 and a second valve 40, configured in a manner such that the filter assembly connects to the production system 20 in two places, such as by the piping 32. A third valve 42 may be included in the algae production system 20 between the places to which the filter assembly 38 connects to the remainder of the algae production 20 such that water flowing through the algae production system 20 can be diverted through the filter assembly 38 by closing the third valve 42 and opening the second valve 40 or such that water flowing through the algae production system 20 can bypass the filter assembly 38 by opening the third valve 42 and closing the second valve 40. In addition, the amount of water flowing through the filter assembly 38 can be controlled by partially opening the second valve 40 and third valve 42. The harvesting assembly can also include a pump or other mechanism capable of diverting water from the algae production system 20 through the filter assembly 38.

In an embodiment, the filter assembly 28 includes one or more filters (not shown) that are configured such that the filter assembly allows the passage of water through the filter but not the passage of algae through the filter. In this manner, the harvesting assembly 28 can be used to harvest algae from the algae production system 28 by collecting algae trapped by the filter assembly 28. For example, an assembly including a filter and a wiper arm is used in accordance with an embodiment. In this embodiment, the wiper arm can sweep across an upstream side of the filter, thereby diverting algae blocked by the filter to a location away from the filter where the algae can be collected. Generally, the harvesting assembly 28 may or may not include filters, but can be any mechanism capable of extracting algae from a fluid.

Figure 2:
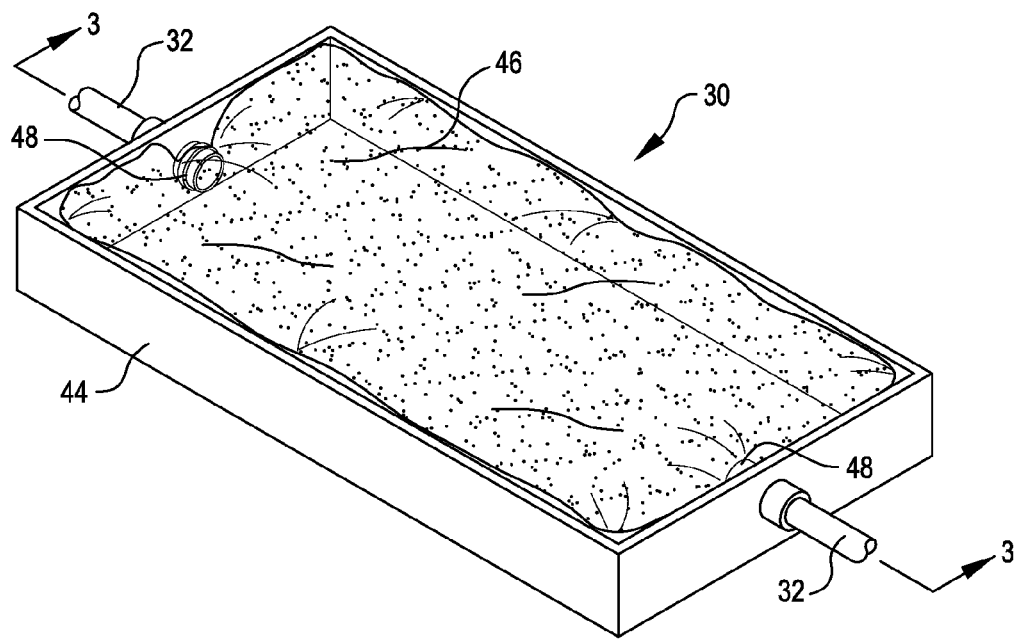
FIG. 2 shows a side-perspective view of a raceway used with the algae production system in accordance with an embodiment.

FIG. 2 shows the raceway assembly 30 in more detail. In an embodiment, the raceway assembly 30 includes a sloped chute 44 through which a photosynthesis channel 46 extends, although the chute 44 need not be sloped, but can be level or have portions that are sloped and portions that are level. In an embodiment, chute 44 is an open rectangular box formed from a series of 4'×8' sheets of plywood, laid out end-to-end, and surrounded by a series of 2"×6" boards extending lengthwise around the sheets of plywood so as to form a fence around the sheets of plywood. In an embodiment, the raceway assembly 30 is ninety-six feet long and approximately six inches high, although it can have other dimensions and it need not be in the shape of a rectangular box. Generally, the chute 44 is any structure configured to contain a photosynthesis channel 46. For example, the chute can be a rectangular box formed from concrete or from another material, a box dug into the ground, or any other suitable structure. In some embodiments the chute 44 has a plurality of bends such that fluid passing through the chute 44 changes direction several times while travelling from one end of the chute 44 to the other. In various embodiments, the chute 44 may be omitted, such as where the photosynthesis channel 46 is formed from a material strong enough such that lateral support is not necessary.

The photosynthesis channel 46, in accordance with an embodiment, is a long tube of transparent material, such as polyethylene, that extends through the chute 44 and is connected to portions of the piping 32 that extend through opposing ends of the chute 44. The photosynthesis channel 46 may be resistant to the passage of one or more types of ultraviolet light, but may allow the passage of other light so as to enable photosynthesis of algae contained in the algae production system 20. For instance, in an embodiment, a UV stable polyethylene tube or tube of other material that allows most of the visible and near infrared spectrum of light to pass through is used. Other materials can also be used for the photosynthesis channel 46. Polyethylene, however, provides an example that is relatively available and inexpensive, providing a simple alternative for replacement. Thus, if algae sticks to the inner surface of a polyethylene tube over a period of time so that the algae blocks too much light, the polyethylene tube can be removed and replaced quickly and inexpensively. One or more valves (not shown) for isolating the polyethylene tube from the remainder of the algae production system 20 can be used. As examples of alternative structures that can be used for the photosynthesis channel 46, the photosynthesis channel can be a clear polyvinyl chloride (PVC) pipe or series of such pipes, a tank with a transparent lid or other component, or generally any structure through which water can flow and through which light suitable for photosynthesis by the algae in the algae production system 20 can pass. In alternate embodiments, fluid flows through the chute 44 or other structure and a suitable transparent or semi-transparent cover, such as a UV-resistant semi-transparent polyethylene sheet, covers the chute 44 or other structure.

Figure 3:
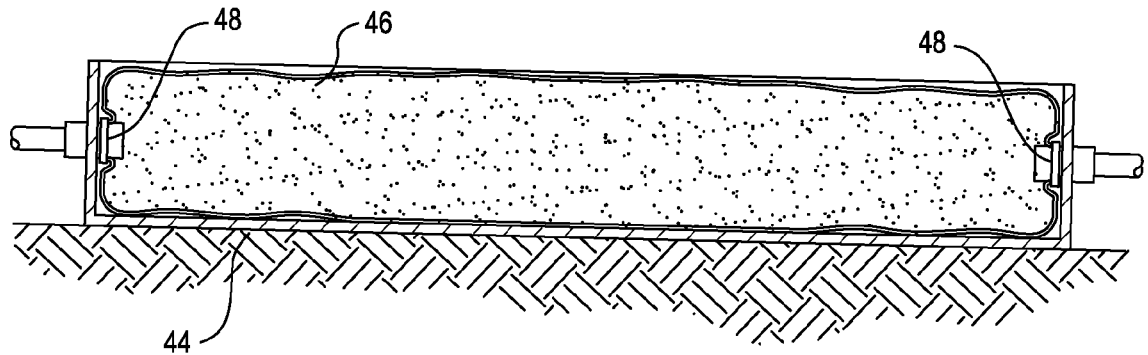
FIG. 3 shows a sectional view of the raceway of FIG. 2 taken along the section lines 3-3 of FIG. 2.

As shown in FIG. 3, in an embodiment, the photosynthesis channel 46 is filled with an algae-containing fluid such that the photosynthesis channel 46 fills the interior space defined by the chute 44 and is supported by the walls of the chute 44. A clamp 48 or other mechanism can be used to provide a water-tight seal between the piping 32 and the photosynthesis channel 46 on each end of the photosynthesis channel 46. As the photosynthesis channel 46 is transparent or semitransparent, the algae inside the photosynthesis channel 46 can store energy through the process of photosynthesis. Further, as discussed above, because the fluid in the algae production system 20 is circulated, the fluid inside the photosynthesis channel 46 has algae generally evenly dispersed throughout, thereby allowing light passing into the photosynthesis channel to be used by substantially all the algae in the photosynthesis channel.

In an embodiment, the photosynthesis channel is the only component of the algae production system 20 through which a significant amount of light for photosynthesis by the algae is able to pass, although other components can also allow or provide light for photosynthesis. By including portions of the system through which a significant amount of light suitable for photosynthesis cannot pass, the photo period (amount of time algae is exposed to light) of the algae is controlled by the rate of flow of fluid through the algae production system 20 (in an embodiment, 100 gallons per minute for a 5,000 gallon system) and/or the amount of the fluid exposed to light. Manipulating the photo period can result in greater mass growth of algae and, as a result, better hydrocarbon yields from the algae. Thus, it should be understood that the photo period of the algae can be varied based on various factors such as, the amount of sunlight available at a particular time, the flow rate of the fluid solution, and the species of algae used.

The raceway assembly 30 can also include other components. For instance, a removable cover (not shown) can be included such that the amount of sunlight entering the photosynthesis channel 46 can be controlled through placement of the removable cover, which can be transparent or semi-transparent. In this manner, less light can be allowed to reach the photosynthesis channel 46 when the sun provides too much energy for the algae production system 20 and more light can be allowed to reach the photosynthesis channel 46 on days when the sun is blocked, such as by clouds. Mirrors and/or lenses can be utilized to direct sunlight into the photosynthesis channel and various structures can be utilized to provide a shadow over the photosynthesis channel. As another example, energy storage devices, such as batteries, can be used in connection with suitable lamps in order to provide light to the photosynthesis channel in addition to the sun, at times when the sun does not provide light, such as at night or during a particularly cloudy day, or to provide light at specific wavelengths that promote optimal algae growth. The energy storage devices can be powered, for instance, by solar cells or other devices. Mechanisms providing control over the amount of sunlight reaching the photosynthesis channel 46 can be manually controlled, or can be part of an automated system, such as a system that uses one or more sensors, such as temperatures sensors and/or photo sensors and includes a processor configured to analyze data from the sensors.

It should also be understood that, while FIG. 1 shows a single raceway assembly 30, the algae production system 20 can include multiple raceway assemblies which can be included in the algae production system 20 in parallel, in series, or both. Further, FIG. 1 shows the raceway assembly 30 having a substantially box-like shape, the raceway assembly 30 can have other shapes, such as serpentine, spiral, or other shapes.

Figure 4:
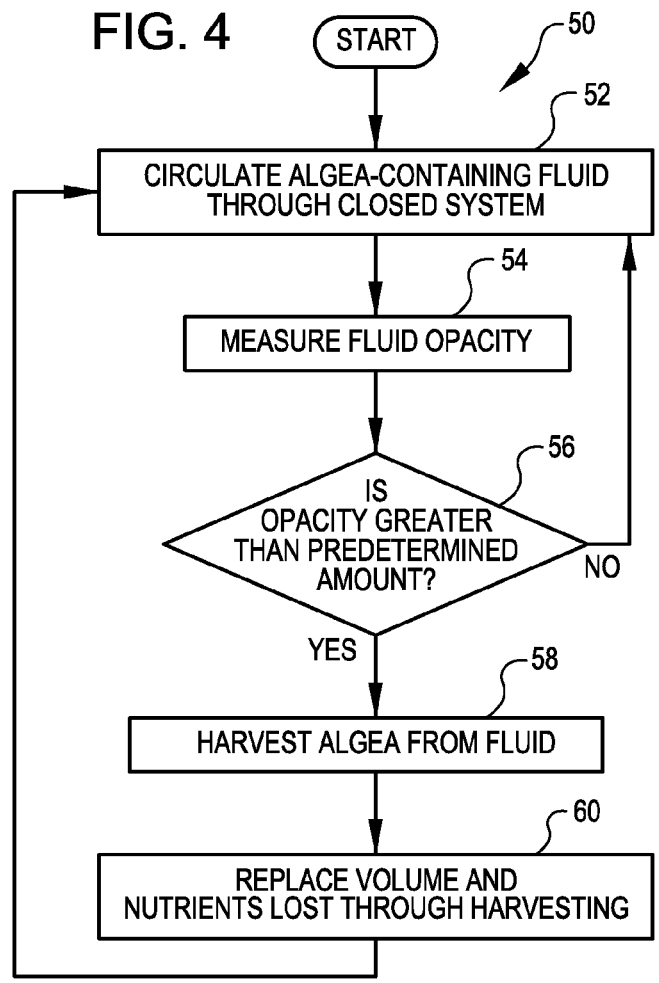
FIG. 4 shows a flowchart demonstrating an algae production method in accordance with an embodiment.

FIG. 4 shows an algae production method 50 in accordance with an embodiment. For example, the algae production method 50 can utilize the algae production system 20 shown in FIG. 1, a variation thereof, or generally any suitable algae production system. Thus, at a circulation act 52, algae-containing fluid is circulated through a closed system, such as the algae production system 20, described above. It should be understood that the circulation act 52 can be an act that is performed continuously while the remaining acts described below are completed, or the circulation act 52 can be a discreet act which is completed before one or more of the remaining acts are completed. The circulation act 52 can also be continuous at times, while discrete at other times.

At an opacity measuring act 54, the opacity of the fluid in the closed system is measured. The term "opacity" as used herein refers to a measurement of the amount of light energy absorbed by the fluid. Thus, the opacity can be measured by comparing the intensity of a light beam before and after passing through a certain dimension of fluid, such as through 10 cm of fluid. Generally, the greater concentration of algae in the fluid the greater the opacity of the fluid will be because the algae absorbs a portion of light passing through the fluid. Therefore the opacity of the fluid can be used as an indicator when to harvest algae from the closed system. Accordingly, at an opacity comparison act 56, a determination is made whether the opacity is greater than a predetermined amount.

In an embodiment, the opacity measurement act 54 and opacity comparison act 56 is performed manually, for example, by extracting fluid from the system and using a kit or laboratory to measure the fluid's opacity. However, it should also be understood that one or both of the opacity measurement act 54 and opacity comparison act 56 can be performed through automated means, such as an opacity sensor (which may comprise one or more photosensors and a lamp) included in the system and a processor configured to process information from the opacity sensor. Further, measurements other than opacity can be used that indicate the concentration of algae in the closed system can be used. As an example, a measurement of the transparency of the fluid can be used.

If it is determined that the opacity comparison act 56 is not greater than a predetermined amount, the fluid is circulated through the closed system some more until the opacity is measured again. If, however, the opacity is greater than a predetermined amount, algae is harvested from the system at a harvesting act 58. For example, in the algae production system 20 shown in FIG. 1, the harvesting act 58 can include closing the third valve 42 and opening the second valve 40 so that fluid circulating to the algae production system 20 passes through the filter assembly 38 which allows algae to be extracted from the fluid of the algae production system 20.

It should be understood that the opacity measuring act 54 and the opacity comparison act can be omitted and that the harvesting act 58 can be performed continuously while fluid is circulated through the closed system. However, because harvesting algae requires the expenditure of energy, using measurements of the fluid's opacity allows algae to be harvested at an optimal time so that an optimum or close-to-optimum amount of algae harvested per unit of energy expended is achieved.

It should also be understood that other characteristics of a closed system can be measured to provide an indication of when to harvest algae from the closed system. For instance, in a closed system in which algae is harvested using a filter, the flow of water through the filter is affected by the amount of algae blocked by the filter such that, as the amount of algae blocked by the filter increases, the rate of fluid flowing through the filter decreases unless the pressure provided by a pump increases. Therefore, measurements of the flow of fluid through the filter or of the strain of a pump used to compensate for the reduced flow through the filter can be used in addition to or as an alternative to measuring the opacity of the fluid in order to determine when to harvest algae from the closed system. Generally, any way of measuring a characteristic of the closed system in order to determine when algae should be harvested can be used.

Returning to FIG. 4, because harvesting algae from the fluid includes removing matter from the closed system, water volume and nutrients lost through the harvesting, in an embodiment, are replaced at a reconstitution act 60. Replacing volume and nutrients lost in harvesting can include opening the first valve 36 and injecting water containing nutrients lost in harvesting into the algae production system 20 or by opening a port in a tank of the algae production system 20 and dropping the nutrients into the port. The nutrients can be from one or more from a variety of sources. For example, in an embodiment, oil is extracted from harvested algae, leaving a mass of cellulose. As is known, the cellulose can be processed in a bio-digester in order to make methane. The process of digesting cellulose in a bio-digester leaves a sludge that can be placed into the closed system in order to feed the living algae in the system. Other nutrients, which can be determined based on the particular species of algae used in the closed system, can be added in addition to or as an alternative to the aforementioned sludge. For example, a source of carbon for the species of algae used may be introduced into the system in order to make up for carbon in harvested hydrocarbons harvested from the system. As an example, air or water having carbon dioxide may be introduced into the system for species of algae that utilize carbon dioxide, and other sources of carbon may be introduced as appropriate for the particular species in the system. Other additives for purposes other than introducing additional carbon into the system may be used as well.

Once the volume of nutrients lost in harvesting has been replaced, the algae production method 50 proceeds to the circulation act 52, which, in an embodiment, includes beginning to circulate algae-containing fluid through the closed system again or, in alternate embodiments, includes simply continuing the circulation of fluid through the closed system. In this manner, the algae production method 50 (and/or any of the methods, or combinations of methods disclosed herein) can be performed in a manner such that the closed system produces algae in an equilibrium or near-equilibrium state in which algae is continuously harvested from the system at a rate approximately equal to the rate at which algae is produced in the system. Various components of an algae production system can be controlled to ensure that the system performs optimally.

Accordingly, FIG. 5 shows a continuous algae production method 62 in accordance with an embodiment. At a circulation and diversion act 64, algae-containing fluid is circulated through a system while a portion of the fluid is diverted through an algae harvester, such as through the harvesting assembly 28 of FIG. 1. Diversion of a portion of the fluid through the algae harvester can be accomplished in various ways. For example, referring to the example of FIG. 1, the third valve 42 can be partially closed while the second valve 40 is partially opened, such that a portion of the fluid circulating through the algae production system 20 passes through the harvesting assembly 28, while the remaining fluid bypasses the harvesting assembly 28. Valves can be manual valves or powered valves. In this manner, the amount of fluid passing through the harvesting assembly 28 can be controlled by changing the amounts that the second valve 40 and the third valve 42 are opened. In other embodiments, the harvesting assembly 28 may include one or more pumps that push and/or pull fluid from the remainder of the algae production system 20. It should be understood that the circulation and diversion act 64 can be a discreet act, a act that is performed continuously while the remaining acts are performed, or a act that is at times continuously performed and at other times discretely performed.

At an opacity checking act 66, the opacity of the fluid of the closed system is measured. Thus, the opacity checking act 66 can be identical or similar to the opacity measurement act 64, described above. At an opacity analysis act 68, a determination is made whether the opacity of the fluid is within an acceptable range. If the opacity is too high, indicating that the closed system has too much algae in the fluid (such as if the rate of algae production would be higher with lower concentration of algae or if a harvester can harvest a larger amount of algae per unit of energy expended), the portion of the fluid diverted through the algae harvester is increased at a diversion-increase act 70 and fluid is continued to circulate through the closed system at the circulation and diversion act 64. However, if it is determined at the opacity analysis act 68 the opacity is too low (such as if a harvester is expending too much energy per unit volume of algae harvested or if a higher concentration of algae would result in a better rate or algae production), then the portion of fluid diverted through the algae harvester is reduced at a diversion-decrease act 72. After the portion of fluid diverted through the algae harvester is reduced, the fluid is circulated through the closed system at the circulation and diversion act 64. Likewise, if it is determined that the opacity analysis act 68 that the opacity is in fact in an acceptable range, the portion of fluid diverted through the algae harvester may be left unchanged and fluid can continue to be circulated through the closed system at the circulation and diversion act 64. In this manner, more algae is harvested from the closed system if the opacity is too high and less algae is harvested from the closed system if the opacity is too low so that algae can continue to grow in the closed system.

As another example of how an algae production system can be controlled to function optimally, FIG. 6 shows a temperature controlled algae production method 74 in accordance with an embodiment. At a fluid cycling act 76, algae-containing fluid is circulated through a closed system. The algae cycling act 76 can be identical or similar to the circulation act 52 described above in connection with FIG. 4.

The temperature of the fluid is measured at a temperature measuring act 78. It should be understood that if fluid temperature can be measured manually or through automated means, such as by a temperature sensor which continuously or periodically senses the temperature of the fluid. Further, the temperature can be measured continuously as the fluid is being circulated, at discrete time intervals, or in any other manner.

At a temperature comparison act 80, a determination is made whether the temperature is within an acceptable range. In an embodiment, an acceptable range is a range of temperatures in which the algae in the fluid is able to live and reproduce. Other ranges may also be used, such as a narrower range corresponding to rates of algae growth considered to be optimal. It should be understood that various species of algae reproduce and are able to live at various temperatures. It should also be understood that the temperature comparison act 80 can be performed manually or through automated means, such as by use of a processor configured to process information received from a temperature sensor.

If it is determined at the temperature at the comparison act 80 that the temperature of the fluid is too low, the amount of sunlight reaching the fluid is increased at a sunlight increase act 82. In this manner, the energy from the sun is allowed to raise the temperature of the fluid. The amount of sunlight reaching the fluid can be increased through devices, such as opening covers or utilizing lenses and/or mirrors, or in any other suitable manner. In addition, other ways of raising the fluid temperature can be used, such as heaters, thermoelectric devices, or generally any way of transferring heat energy to the fluid. In an embodiment, the sunlight increase act 82 includes removing or partially removing a cover which totally or partially covers the raceway for the raceway assembly 30, described above, in connection with FIGS. 1-3. If it is determined at the temperature comparison act 80 that the temperature of the fluid is too high, such as if the energy introduced into the system by a pump is too much or if sunlight raises the temperature of the fluid too much, the amount of sunlight reaching the fluid is decreased at a sunlight decrease act 84. For example, the sunlight decrease act 84 can include blocking the amount of sunlight reaching the fluid, such as by pulling a cover partially or totally over the raceway assembly 30, described above, in connection with FIGS. 1-3. Further, other ways of reducing the fluid temperature, such as by using refrigeration, using thermoelectric devices, routing fluid underground in a manner transferring heat energy to the ground, or generally any way of removing heat energy from the fluid can be used.

It should also be understood that while the present disclosure describes three separate methods, that acts of the various methods can be combined, that acts can be omitted, and that additional acts can be included. Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A system for producing a hydrocarbon-producing photosynthetic organism, comprising:
   a fluid containing a population of the hydrocarbon-producing photosynthetic organism;
   a closed raceway configured to contain a portion of the fluid and to permit the portion of the fluid to receive light suitable for photosynthesis by the hydrocarbon-producing photosynthetic organism;
   a pump;
   a harvester configured to remove a portion of the population from the fluid; and
   piping fluidly connecting the pump, raceway, and harvester in a circuit such that the pump circulates the fluid through the raceway.

2. The system of claim 1, further comprising a first tank fluidly connected to the piping.

3. The system of claim 2, further comprising a second tank fluidly connected to the piping, the second tank at a lower elevation than the tank.

4. The system of claim 1, wherein the raceway is sloped such that the fluid flows through the raceway in a downhill direction.

5. The system of claim 1, wherein the hydrocarbon-producing photosynthetic organism includes a hydrocarbon-producing microalgae species.

6. The system of claim 5, wherein the hydrocarbon-producing microalgae species survives at a temperature range lethal to native contaminant organisms, and wherein the raceway is configured to collect solar energy to maintain the temperature of at least a portion of the fluid within the temperature range.

7. A system for producing a hydrocarbon-producing photosynthetic organism, comprising:
   a substantially closed conduit system enclosing a fluid, said fluid containing a population of a hydrocarbon-producing photosynthetic organism and said conduit system configured to permit at least a portion of the population to receive light suitable for photosynthesis;
   a fluid-moving mechanism adapted to move the fluid through at least a portion of the conduit system; and
   a harvester adapted to remove at least a portion of the hydrocarbon-producing photosynthetic organisms from the fluid.

8. The system of claim 7, wherein the hydrocarbon-producing photosynthetic organism comprises a microalgae species.

9. The system of claim 8, wherein the microalgae species is heat resistant.

10. The system of claim 7, further including a raceway configured to permit a portion of the population in the raceway to receive light suitable for photosynthesis.

11. The system of claim 10, wherein the raceway includes a polyethylene channel through which the fluid flows.

12. The system of claim 7, wherein the conduit system is substantially opaque.

13. The system of claim 7, including a device to measure the concentration of the population in the fluid and wherein the system is adapted to vary the rate at which the harvester removes said at least a portion of the hydrocarbon-producing photosynthetic organisms, said rate depending on the concentration.

* * * * *